United States Patent
Bommaraju et al.

(10) Patent No.: US 10,812,424 B1
(45) Date of Patent: Oct. 20, 2020

(54) SYSTEM AND METHOD FOR QUANTIFYING MENTAL HEALTH WITHIN A GROUP CHAT APPLICATION

(71) Applicant: Beacon Tech Inc., Newark, DE (US)

(72) Inventors: Satya Prateek Bommaraju, Revere, MA (US); Ravi Akshay Shah, Revere, MA (US)

(73) Assignee: Beacon Tech Inc., Baltimore, MD (US)

( * ) Notice: Subject to any disclaimer, the term of this patent is extended or adjusted under 35 U.S.C. 154(b) by 86 days.

(21) Appl. No.: 16/268,118

(22) Filed: Feb. 5, 2019

Related U.S. Application Data (60) Provisional application No. 62/626,218, filed on Feb. 5, 2018.

(51) Int. Cl.
```
H04L 12/24      (2006.01)
H04L 12/58      (2006.01)
G06N 20/00      (2019.01)
A61B 5/00       (2006.01)
A61B 5/16       (2006.01)
A61B 5/11       (2006.01)
```

(52) U.S. Cl.
CPC .......... *H04L 51/046* (2013.01); *A61B 5/7264* (2013.01); *A61B 5/7275* (2013.01); *A61B 5/743* (2013.01); *A61B 5/746* (2013.01); *G06N 20/00* (2019.01); *A61B 5/1114* (2013.01); *A61B 5/165* (2013.01); *A61B 2562/0219* (2013.01)

(58) Field of Classification Search
CPC ..... H04L 51/046; A61B 5/7264; A61B 5/746; A61B 5/7275; A61B 5/743; A61B 5/1114; A61B 2562/0219; A61B 5/165; G06N 20/00
USPC .......................................................... 709/206
See application file for complete search history.

(56) References Cited

U.S. PATENT DOCUMENTS

| | | | |
|---|---|---|---|
| 2015/0256675 A1* | 9/2015 | Sri | H04L 12/1827 379/265.09 |
| 2016/0140320 A1* | 5/2016 | Moturu | G06F 19/3418 434/236 |
| 2016/0359777 A1* | 12/2016 | Tucker | H04L 51/16 |
| 2017/0004269 A1* | 1/2017 | Potter | G06N 20/00 |
| 2017/0249437 A1* | 8/2017 | Jain | G16H 50/30 |
| 2018/0145935 A1* | 5/2018 | Blokhin | H04L 51/02 |
| 2018/0308574 A1* | 10/2018 | Proctor Beauchamp | G06F 19/3418 |
| 2019/0037046 A1* | 1/2019 | Orbach | H04L 67/306 |
| 2019/0052584 A1* | 2/2019 | Barve | H04L 51/02 |
| 2019/0102706 A1* | 4/2019 | Frank | G06K 9/6256 |

\* cited by examiner

*Primary Examiner* — Moustafa M Meky
*Assistant Examiner* — Elizabeth Kassa
(74) *Attorney, Agent, or Firm* — Morse, Barnes-Brown & Pendleton, P.C.; Sean D. Detweiler, Esq.

(57) ABSTRACT

A method and apparatus for quantifying the health status of users of a group chat. The scores are generated based on message in a group chat indicating the relative health of groups and individual users in the groups. The generated scores are provided in a display of a graphical user interface, enabling a moderator to more effectively monitor and manage a number of groups and users.

14 Claims, 8 Drawing Sheets

SYSTEM AND METHOD FOR QUANTIFYING MENTAL HEALTH WITHIN A GROUP CHAT APPLICATION

CROSS-REFERENCE TO RELATED APPLICATION(S)

This application claims priority to, and the benefit of, U.S. Provisional Application 62/626,218 filed Feb. 5, 2018 for all subject matter common to both applications. The disclosure of said provisional application is hereby incorporated by reference in its entirety.

FIELD OF THE INVENTION

The present invention relates evaluating mental health of subjects via their communications. In particular, the present invention relates to a system and method to quantify the mental health (in the form of a behavioral sentiment score) of all the users within a group chat application.

BACKGROUND

One in five of all American adults are diagnosed with a mental health problem and two out of three of those adults receive zero care. While therapy is effective at treating many conditions, social stigma and physical barriers to care mean that many patients utilize therapy inconsistently, or not at all. Providers are also handicapped by a lack of persistent patient monitoring and incomplete patient histories. A significant percentage of these people instead use anonymous websites to talk about their problems. Unfortunately, these websites are plagued by toxicity and trolling, i.e., intentional maliciousness by other users.

To address this issue a mobile application for text based peer support that allows patients within chat groups to talk anonymously about their problems from anytime and anywhere was built. These groups are overseen by moderators (who are therapists, trained peer support specialists, case managers, etc.) who can step in to provide additional support to the patients or conduct guided therapeutic exercises through the application. However it is practically impossible for a single moderator to read every single message that is posted within the group and keep track of the progress of every user. The way such problems are currently handled in other forums is to increase the number of moderators to cover all the messages that are sent. In addition to being prohibitively expensive, splitting attention across more people means that clinicians have a harder time understanding the overall mental health status of the patients and their progress over time.

SUMMARY

Therefore there exists a need for creating technology that can scale the capabilities of a moderator while also providing clinical insights that can enhance their understanding of the patient's health.

The present invention provides means to empower moderators within a group in at least the following practical applications:

Triaging patient risk such that they can prioritize their attention on the patients who need the most attention;
Tracking the mental health status of patients over time to show patient progress, and using that to forecast future information;
Analyzing conversations within the group to compute an overall estimate of group health; and
Identifying therapeutic interventions that help drive patient improvement.

In accordance with an exemplary embodiment of the present invention, a method for quantifying mental health for user in a group chat is provided. The method includes receiving, at a hosting site, a message from a user in a group chat on a client device; processing, at the hosting site, the received message using a message model to generate a message score; processing, at the hosting site, the received message, the generated message score, historical data for the user, and user attributes using a user model to generate a user score; processing, at the hosting site, the received message, the generated message score, the generated user score, historical data for the group chat, and group attributes using a group model to generate a group score; determining, at the hosting site, if a moderator needs to be alerted based on the generated message score, generated user score, and generated group score; and providing to a moderator, a graphical interface indicating the generated message score, generated user score, and generated group score.

In accordance with aspects of the present invention, the method can further include generating, at the hosting site, a user score forecast base on generated user score and generated group score; and providing the generated forecast to the moderator as part of the graphical interface.

In accordance with aspects of the present invention, the method can further include receiving, at the hosting site, an indication that a message has been flagged; determining, at the hosting site, if the flagged message is a message that led to a determination that a moderator need to be alerted; and updating models if flagged message did not result in moderator being alerted.

In accordance with aspects of the present invention, the historical data for the user can include previous messages from the user, the corresponding user scores for the messages, and message feature vectors for the messages used in generating the user scores.

In accordance with aspects of the present invention, the historical data for the group chat can include previous messages for all the users in a group, the corresponding messages scores, message feature vectors for the messages used in generating the user scores, and the resulting group scores.

In accordance with aspects of the present invention, the step of generating a message score can include applying a group of one or more transformations to the message to generate a set of one or more vectors pertaining to the message; concatenating the set of vectors pertaining to the vector into a message feature vector; and applying a classifier to the message feature vector to generate a message score. In certain embodiments, the step of applying a group of one or more transformations to the message can further include applying a first group of one or more transformations to the message to generate a first set of one or more vectors pertaining to the message; concatenating the first set one or more vectors pertaining to the message into a first feature vector; applying a second group of one or more transforms to the first feature vector to generate a second set of one or more vectors pertaining to the message; and concatenating the second set one or more vectors pertaining the message into a message feature vector.

In accordance with aspects of the present invention, generating a user score can include applying one or more transformations on the message, message score, and user history to generate a set of one or more vectors pertaining to the user; concatenating the set of vectors pertaining to the user to generate a user attributes vector; and inputting the message, message score, user history, and user attributes vector into a sequence prediction model to generate a user score.

In accordance with aspects of the present invention, the generating a group score can include applying one or more transformations on the message, message score, user score, and history of group to generate a set of one or more vectors pertaining to the group; concatenating the set of vectors to generate a group attributes vector; and inputting the message, message score, group history, and group attributes vector into a sequence prediction model to generate a group score.

In accordance with another exemplary embodiment of the present invention, a system for quantifying mental health for user in a group chat is provided. The system includes a hosting site comprising a storage for storing messages from users and data associated with messages. The hosting site operable to receive a message from a user in a group chat on a client device; process the received message using a message model to generate a message score; process the received message, the generated message score, historical data for the user, and user attributes using a user model to generate a user score; process the received message, the generated message score, the generated user score, historical data for the group chat, and group attributes using a group model to generate a group score; determine if a moderator needs to be alerted based on the generated message score, generated user score, and generated group score; and provide to a moderator, a graphical interface indicating the generated message score, generated user score, and generated group score.

In accordance with aspects of the present invention the hosting site is further operable to generate a user score forecast based on generated user score and generated group score; and provide the generated forecast to the moderator as part of the graphical interface.

In accordance with aspects of the present invention the hosting site is further operable to receive an indication that a message has been flagged; determine if the flagged message is a message that led to a determination that a moderator needs to be alerted; and update models if flagged message did not result in moderator being alerted.

BRIEF DESCRIPTION OF THE FIGURES

These and other characteristics of the present invention will be more fully understood by reference to the following detailed description in conjunction with the attached drawings, in which.

DETAILED DESCRIPTION

Illustrative embodiments of the present invention relates to a method and system for quantifying the health status of users of a group chat. A score is generated based on message in the group chat indicating the relative health of groups and individual users in the groups. The generated scores are displayed in a graphical user interface, thereby enabling a moderator to more effectively monitor and manage a number of groups and users.

FIG. 1 through FIG. 8, wherein like parts are designated by like reference numerals throughout, illustrate an example embodiment or embodiments of a system and methodology for quantifying the mental health (in the form of a behavioral sentiment score) of all the users within a group chat application, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Figure 1:
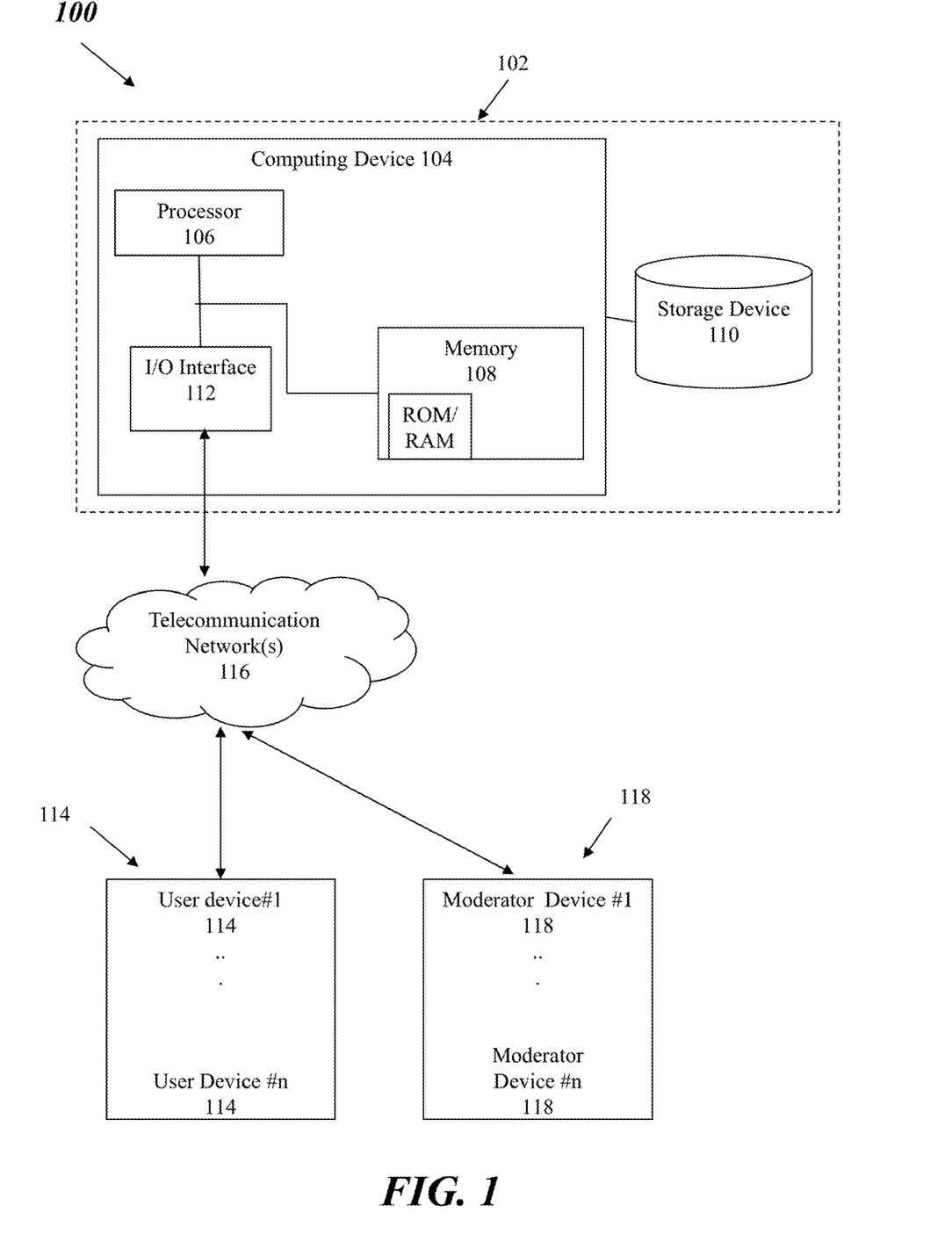
FIG. 1 is a diagrammatic illustration of a system for quantifying mental health in a group chat environment in accordance with the aspects of the invention.

FIG. 1 depicts a high-level system architecture of implementing processes in accordance with aspects of the present invention. Specifically, FIG. 1 depicts a computing system 100 including a hosting site 102 including a computing device 104 having a processor 106, a memory 108, storage 110, and an input/output interface 112. The hosting site 102, including the computing device 104, may be a general purpose computer or a specialized computer system. For example, the computing device 104 may include a single computing device, a collection of computing devices in a network computing system, a cloud computing infrastructure, or a combination thereof, as would be appreciated by those of skill in the art. In accordance with example embodiments, the computing device 104 may be a server system in communication with a database (e.g., storage device 110). Similarly, as would be appreciated to one of skill in the art, the storage device 110 may include any combination of computing devices configured to store and organize a collection of data. For example, the storage device 110 may be a local storage device on the computing device 104, a database storage component of hosting site 102, a remote database facility, or a cloud computing storage environment. The storage device 110 may also include a database management system utilizing a given database model configured to interact with a user for analyzing the database data.

The computing system 10 of FIG. 1 may further include a plurality of user devices 114 and moderator devices 118, each executing software such as the group chat software or application or an internet browser providing access to the group chat. The primary difference between the user device 114 and the moderator device being that the moderator is provided with a graphical interface displaying the quantitative health scores of the users and/or groups being moderated by the moderator. Similar to the computing device 104, the user devices 114 and moderator devices 118 may each include a single computing device, a collection of computing devices in a network computing system, a cloud computing infrastructure, or a combination thereof, as would be appreciated by those of skill in the art.

Figure 2:
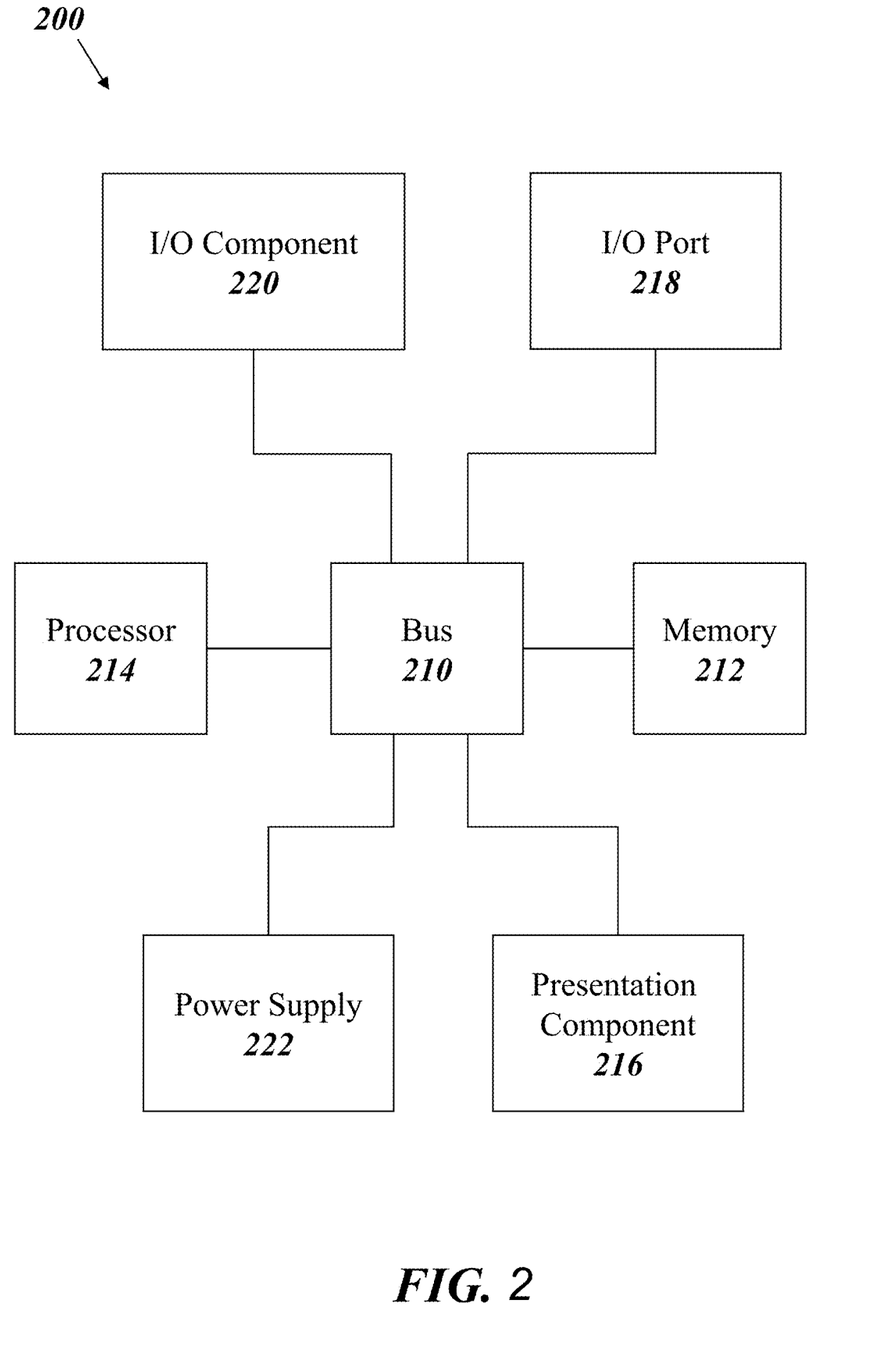
FIG. 2 is a diagrammatic illustration of a high level architecture for devices implementing processes in accordance with the aspects of the invention.

Any suitable computing device can be used to implement the computing devices 104, user device 114, and moderator device 118 and methods/functionality described herein. One illustrative example of such a computing device 200 is depicted in FIG. 10. The computing device 200 is merely an illustrative example of a suitable computing environment and in no way limits the scope of the present invention. A "computing device," as represented by FIG. 2, can include a "workstation," a "server," a "laptop," a "desktop," a "hand-held device," a "mobile device," a "tablet computer," or other computing devices, as would be understood by those of skill in the art. Given that the computing device 200 is depicted for illustrative purposes, embodiments of the present invention may utilize any number of computing devices 200 in any number of different ways to implement a single embodiment of the present invention. Accordingly, embodiments of the present invention are not limited to a single computing device 200, as would be appreciated by one with skill in the art, nor are they limited to a single type of implementation or configuration of the example computing device 200.

The computing device 200 can include a bus 210 that can be coupled to one or more of the following illustrative components, directly or indirectly: a memory 212, one or more processors 214, one or more presentation components 216, input/output ports 218, input/output components 220, and a power supply 224. One of skill in the art will appreciate that the bus 210 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 2 is merely illustrative of an exemplary computing device that can be used to implement one or more embodiments of the present invention, and in no way limits the invention.

The computing device 200 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 200.

The memory 212 can include computer-storage media in the form of volatile and/or nonvolatile memory. The memory 212 may be removable, non-removable, or any combination thereof. Exemplary hardware devices are devices such as hard drives, solid-state memory, optical-disc drives, and the like. The computing device 200 can include one or more processors that read data from components such as the memory 212, the various I/O components 216, etc. Presentation component(s) 216 present data indications to a user or other device. Exemplary presentation components include a display device, speaker, printing component, vibrating component, etc.

The I/O ports 218 can enable the computing device 200 to be logically coupled to other devices, such as I/O components 220. Some of the I/O components 220 can be built into the computing device 200. Examples of such I/O components 220 include a microphone, joystick, recording device, game pad, satellite dish, scanner, printer, wireless device, networking device, and the like.

Figure 3:
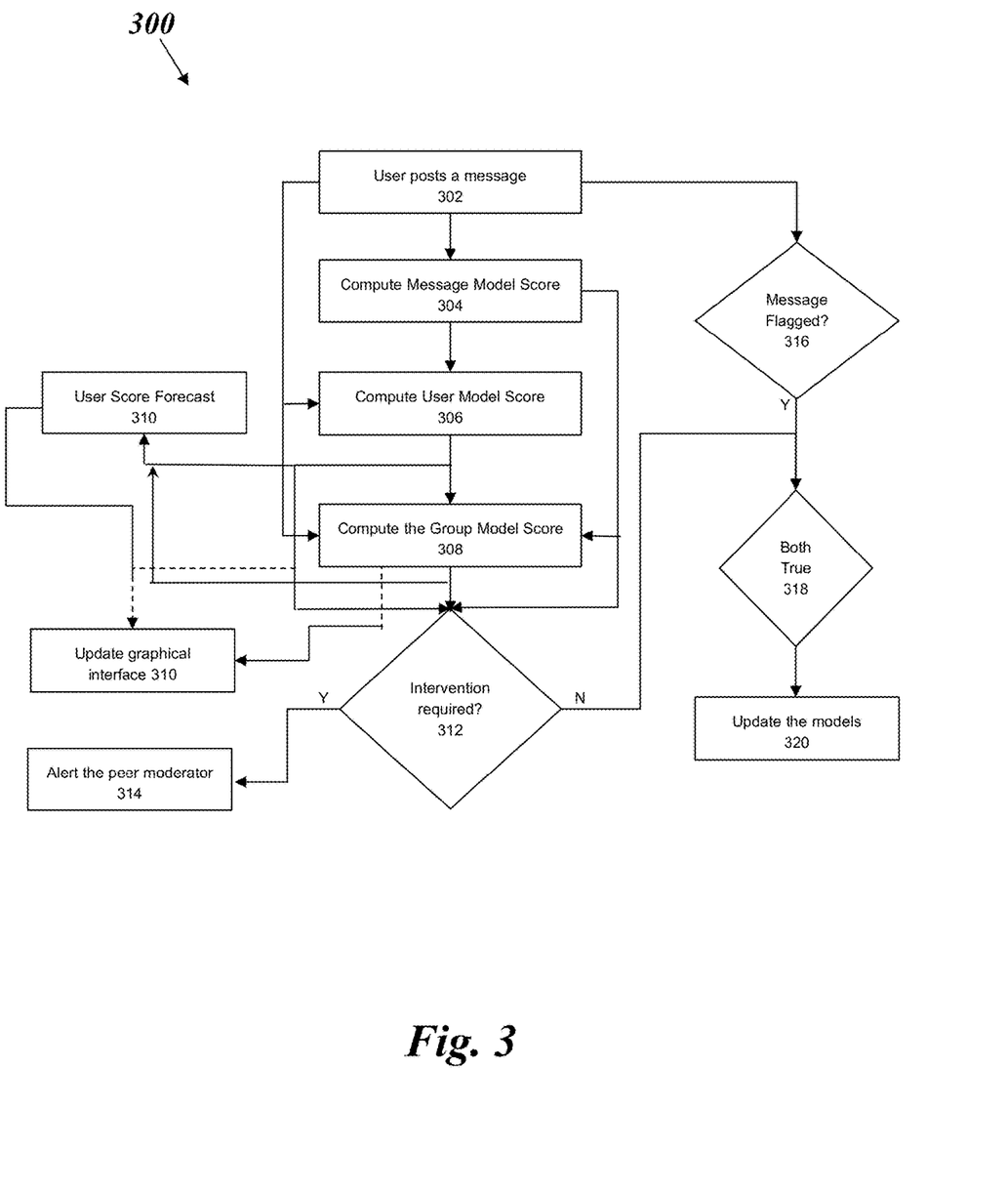
FIG. 3 is a flowchart that depicts the various components in the system and how they interact with each other in accordance with one embodiment of the invention.

The functionality of the present invention is provided by the system and hardware of FIGS. 1-2 through the execution of software that makes the hardware perform in the desired manner. FIG. 3 depicts flow diagram 300 of one possible implementation of software processes, represented as blocks 302-322, operating on the hosting site 102 of FIG. 1 to provide a system that can monitor and report on health for users of a group chat in accordance with aspects of the present invention.

In operation, a user device 114 is used to connect to the group support session and to post messages which are received at the hosting site 102 (block 302). Each message 304 first gets analyzed by the message model to generate a message score for the message (block 304). This message score represents a quantified indication of mental health pertaining to the message. A low or negative message score is something that signifies negative emotional sentiment such as maliciousness or depression while a higher score represents positive emotions such as hope, encouragement or recovery.

The message score computed by the message model is then used as an input to the user model along with the message to compute a user model score (block 306). This user model score represents the overall mental health state of the user and is used to triage patient risk in the graphical interface for the moderators.

This user model score, the message model score and the message itself are then used as inputs to the group specific model which computes the group model score (block 308). The group model score represents the overall mental health state of the group in and of itself and can aid moderators in determining at a single glance if the peer group is functioning or not.

In certain embodiments, the user model score and the group moderator score are then used to compute a forecast for the mental health scores of each user in the future (block 310). The scores computed are the prediction of their mental health 7 days into the future, 30 days into the future and 90 days into the future and are displayed in the graphical interface.

Then all three scores are used to determine whether the therapist or peer moderator should be alerted (block 312). This alert (block 314) is for cases where the scores indicate that the users are at critical risk of suicide, self-harm or relapse.

In some embodiments, users within the group also have the ability to manually flag messages as being negative or toxic (block 316). If a message was flagged by the user but the models fail to identify it (block 318), then that message becomes a new data point for the system (block 320). This feedback loop allows the models to learn from mistakes and grow smarter over time.

The user model score, the group model scores, and the user score forecasts are passed to the graphical interface that updates the charts to display the latest values (block 322).

The group therapy session consists of a group of users who connect into the group via a user device 114 such as a smartphone or a tablet. Each such group centers on a particular mental health issue such as depression or anxiety, with users within a group all facing the same problem. These groups will also have one or more moderators using, whose credentials range from licensed therapists to peer support specialists, facilitating dialogue between users via a moderator device 118. Users typically would be interacting with each other within the group via messages in the form of text, emoticons, gif images via a gif keyboard, images, urls, or voice recordings. These range from generic conversation and banter to descriptions of the problems they are facing with their mental illness.

Figure 4:
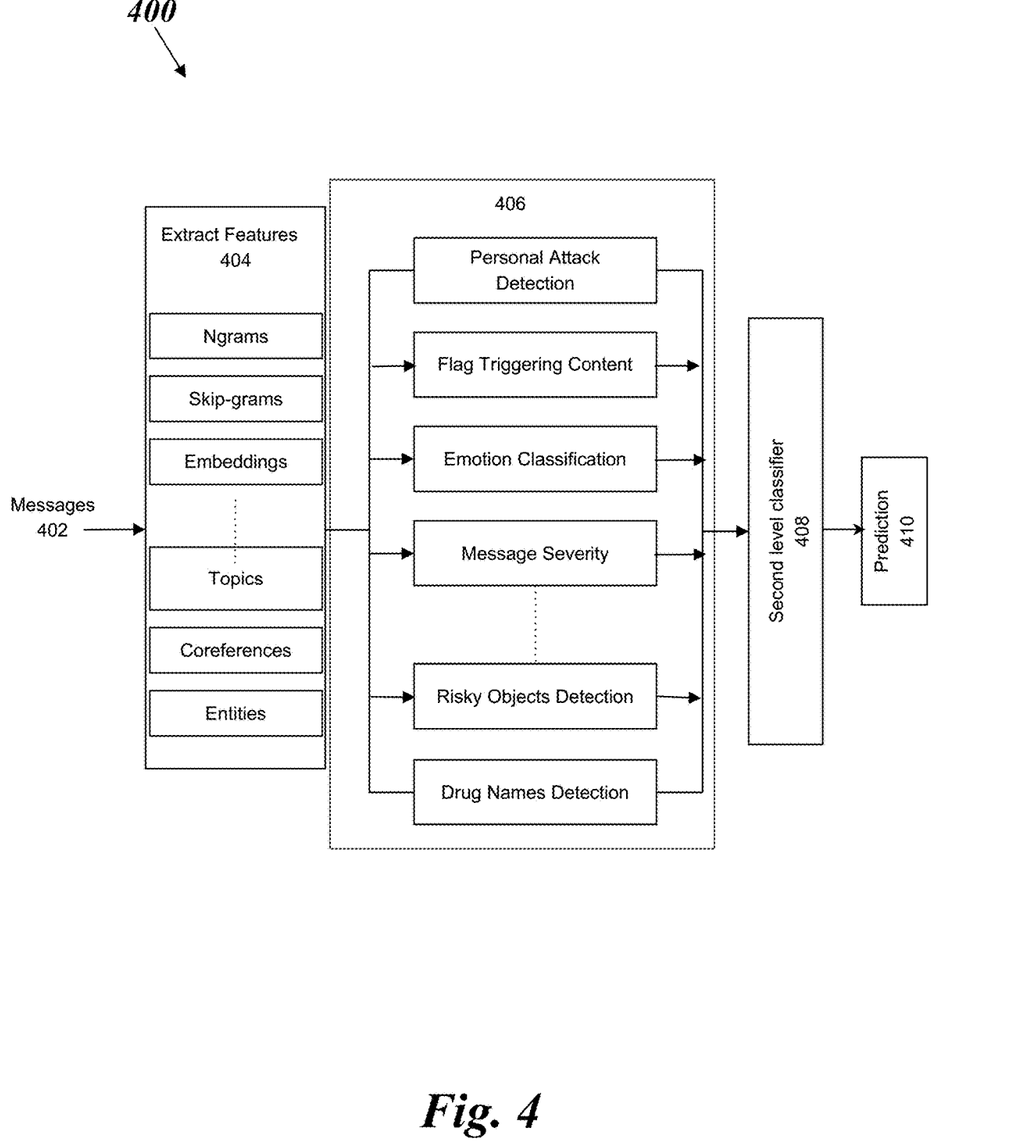
FIG. 4 is a depiction of the Message Model within the system whose purpose is to analyze messages sent by the users and compute a behavioral sentiment score of that message in accordance with one embodiment of the invention.

As set forth in FIG. 3, when a message is posted by a user, it is scored by three separate models. The first is a Message Model 400 that computes a score based on that message alone. FIG. 4 depicts an exemplary Message Model 400 in accordance with one embodiment of the present invention.

When a new message 402 is posted in the group, the Message Model 400 first builds a mathematical representation of that message 402 called a feature vector. This is done by applying a set of transformations 410, 420, in parallel, to the message that convert the text message into a vector and finally concatenating all the vectors into one final message feature vector.

In accordance with one example embodiment, a first set of transforms 404 is applied to extract features of the message 402. The features extracted from the message 402 vary based on the nature of the message 402. If it is a text message then features may include, but are not limited to:
  Word n-grams: A vector built by enumerating all possible n-length word sequences in the English language (computed beforehand by analyzing large text datasets such as entire dumps of the internet) and then listing the counts and frequencies of the sequences present in the text message. The choice of n is optimized beforehand so as to get the best performance.
  Character n-grams: Similar to word n-grams but using n-length sequences of characters instead of words.
  Dependency parses or Skip-grams: Processes the text message to build a tree that highlights the relationships between words. For example in the sentence "I spoke to my therapist" subject of the sentence "I" is related to the object of the sentence "therapist" by the verb "spoke". The tree is built by a previously trained machine learning model that starts with a root token and then iteratively builds the rest of the tree by enumerating all possible extensions to the tree, comparing those enumerations with previously computed possibilities and picking the most frequent one. This tree is then used to build triads of terms such as verb, subject, object and the counts of these triads are used to build a vector.
  Named Entity or Topic Recognition: Entities in the sentence such as names of people, places, dates, objects are identified then entity categories are appended to each word to create new tokens. For example the sentence "John went to New York" would become "John_Person went to New_Location York_Location". Then the word-ngram approach is used to build a feature vector from this.
  Coreference Resolution: Coreference is when two or more words refer to the same person, thing or verb. For example—"I went to church yesterday. It was really grand."
  Other Techniques: Other commonly used transformation methods are low dimensional projections such as matrix factorization, latent semantic analysis, autoencoders, or word embeddings. These Word Embeddings can be any unsupervised word embeddings such as GloVe, word2vec, etc. but also those trained in a supervised setting such as sentiment specific word embeddings. These embeddings are computed by starting from an existing feature vector (such as a word vector, or dependency parse vector) and then training a machine learning model that tries to predict the next word in a sentence given the previous set of words. Because of this the embeddings for each word are spatially related such that words similar in meaning are closer in embedding space.
  Emoticon or Image: Emoticons & gif images from the gif keyboard are already pre-tagged for the emotion that they represent. For example a gif of someone walking out of a meeting and jumping out the window would be tagged with a series of keywords such as # death or # suicide. These keywords are used as features along any additional features extracted from the image by standard image processing techniques such as raw pixel representations, edges, corners, template matching, hough transforms or unsupervised representations from a convolutional autoencoder. The same image processing features would be extracted from any image posted by the user.
  Voice Recordings: In the case that the message was in the form of a voice recording, then the speech would be transcribed into text and all the previous text processing features would be extracted from it. In addition to that standard speech features such as pitch of the speaker, tone, stress levels, etc. would be extracted and used as features.
  Time: The date of the message, the day it was posted, the time of the day it was posted (exact time, as well morning, afternoon, evening or night)
  Extra data: Data from the phone such as accelerometer data (to check if hands are shaking), location data (to check for unsafe locations), light sensor information (to identify if user is posting in the darkness or from outside) as well as click locations (there might be a lot of misclicks if the user is drunk)

The feature vectors resulting from the applied transforms are then concatenated before a second set of transforms 406 are applied to it. These transforms are done by multiple machine learning models that aim to capture contextual and other information relevant to the user's mental health. These include but are not limited to:
  Personal Attack detection—Given a previous corpus of data manually annotated by humans that lists whether a message is a personal attack or not, a statistical model is trained that inputs a feature vector and outputs the probability of the if it being a personal attack or not. Any statistical/machine learning method such linear regression, support vector machines, etc. can be used. Fundamentally what these methods are doing is identifying the words or set of words that are highly correlated with abusive messages and storing that information via another vector. When a new message is posted in the group, this model vector (which is stored in the database) is then compared with the new feature vector to generate the final probability.

Triggering Content detection—This is a machine learning model trained on a corpus of previously annotated data indicating if the content of a message is triggering or not. Such content could be topics discussing suicidal ideation, sexual assault or graphic representations of violence.

Emotion Classifier—This is a machine learning model trained on previous corpus of messages that identify the emotion present in that particular message. Two different emotion classifier models are trained depending if the input is a text message or a voice message.

Mental Health Category Detection—The purpose of this module is to identify the mental health condition that is the topic referenced in the message. In most cases this is the same as the category of the peer group itself (e.g.: if it's a substance use recovery group). However since multiple mental health conditions are often comorbid with each other a user could be talking about depression issues in a substance use condition model as well. The specific condition being discussed is found by the use of a machine learning model that has been trained to identify condition categories. The training data for this is a corpus of messages and human annotations indicating what mental health condition is being discussed. The prediction of this model (a vector of probabilities) for this input is then used as the feature vector.

Risky Objects Detection—This is a context sensitive machine learning model that identifies images or text messages that contain risky objects. Examples of this are messages or images containing depictions of weapons, alcohol, drugs or even locations where people might attempt suicide. These could be buildings, traffic, railway stations and more. A comprehensive database of such objects/places works with the machine learning model to pattern match and also catch synonyms of those words, pronouns that refer to usage of those words in previous messages (e.g.: Message 1—I lost my knife today. Message 2—Oooh I think about mine all the time.)

Drug Names Detection—Compares the message with a database of previously collected drug names (prescription as well as illegal) and their corresponding slang/jargon. The counts of each drug are then used as new feature vectors.

Count of objects reasoning—The objective of this is to identify the number of any particular entity and is done by identifying locations of numbers in the sentence (by checking for Arabic numerals e.g.: 12, as well as names for those numbers e.g.: twelve) and then comparing with a set of precomputed templates that cover the possible variations of number use (e.g.: {Number} of {Entity}, or {Number} {Entities}). The reasoning behind this is to identify if someone took 10 sleeping pills instead of 1 or ten times the dosage of a medicine. This can also be done via a statistical model that is trained a corpus of message data which has been humanly annotated to identify the locations of number-object pairs.

Message Severity Model—This is a structured prediction model that inputs the feature vector of the new message as well as the feature vectors of the previous messages posted with the group to generate a probabilistic score of the severity of the message. The previous messages posted in the group are also considered for the model because a message that might seem harmless when viewed in isolation could be a malicious response within the conversation. For example the sentence "Go ahead" is a perfectly normal message in isolation but if it is the response to someone talking about how they might kill themselves it is extremely malicious in nature. The process to train this model is:
a. Build a corpus of text message data and have humans annotate it for the severity of the message. The severity rating goes from 0 (indicating imminent risk of suicide/self-harm) to 5 (indicating extreme happiness)
b. Define the type of machine learning model to train. This could be a support vector machine, a Conditional Random Field or a Bidirectional Long Short-Term Memory (BiLSTM). BiLSTM models are especially good for this type of problem as they can capture long term context in sequences of text messages.
c. Randomly initialize the coefficients (weights) of the model.
d. Compute the feature vectors of the training data
e. Define a loss function that can be used to estimate the error of the model.
f. Then the model can be trained as:
   i. Let C be a weight vector of length n
   ii. Do until converged:
      1. For each example X in the training set with true output Y:
         a. Make a prediction P for input X given weights W
         b. Compute error between P & Y using the loss function
         c. Update weights W based on the previous error
g. Store the updated model weights W for later use.

Once again the final feature vector is a concatenation of the individually computed features. These features encapsulated in the final feature vector are then used as inputs to the second level classifier 408. The second level classifier 408 could be any classifier such as logistic regression, xgboost, neural network etc. The purpose of the second level classifier 408 is that the message model 400 can dynamically adjust the weights of each individual feature based on the training data. The final prediction score 410 is a vector or length N where N is the number of distinct categories for message severity. Each value of the vector indicates the probability of the prediction belong to that category. The final prediction score 410 is then computed as a weighted combination of those individual probabilities. One such combination method is $$\text{message score} = \sum_{l=0}^{N} l * p_l \text{ where } p_l = \text{probability of message being of severity } l$$

While the example embodiment of the Message Model 400 of FIG. 4 involves two sets of transforms applied successively, it should be understood that one set of transforms or any number of sets of transforms could be applied. In a similar manner, the number of transforms in a set can also vary.

Figure 5:
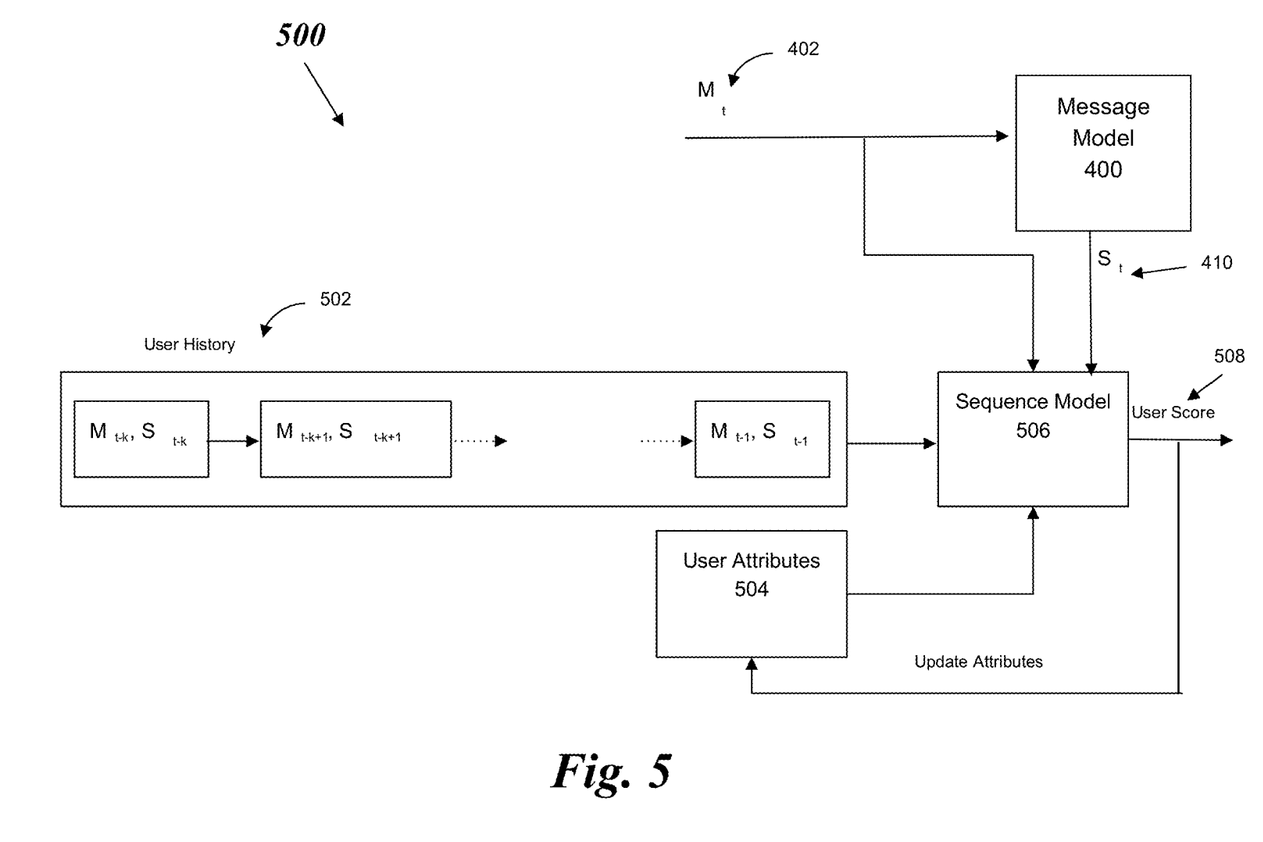
FIG. 5 is a depiction of the User Model within the system whose purpose is to analyze new messages and compute the overall mental health score of each user in the context of their previous messages in accordance with one embodiment.

As indicted in the flow diagram of FIG. 3, the final prediction score 410 generated by the Message Model 400, as well as the original message 402 are provided to a User Model 500 as seen in FIG. 5. The function of the User Model 500 is to compute a score for the overall health of the patient. This user score is used to visualize patient risk in the graphical interface and can help moderators focus attention towards the users who need it more.

Every time a new message 402 is posted in the group by a user the score for each user is updated by the User Model 500. The User Model 500 takes into consideration not just the latest message but also the previous history of messages 502 posted by the user. The way this is done is that for each message posted by a user, a database of user history is maintained of all the messages the user posted along with the message model feature vector and score of that message.

In addition, for every user a persistent set of user attributes 504 are maintained, that is updated every time they post a message. The list of computed user attributes 504 include (but not limited to) the following:

- Histogram of time activity—The time that each message by the user is categorized into 1 of 24 hourly categories (so a message that was posted at 16:23 would fall into bucket 16) and then the total counts of each are noted. This gives the model an estimate of when a user most frequently posts and anomalies such as late night activity can be caught. In addition to this, histograms of other sensor information, such as accelerometer data, light sensor data, and more, is also stored.
- Contribution to group discussion—The N most frequent words (without counting stop works like "and" or "if", etc.) used by all members of a group are used to build an N length vector that, whose values are the counts of the words among them that that were used by the user. This is an estimate of how much a particular user contributes to the overall group discussions as the most frequent words used tend to represent the overall mean of the group's conversations.
- Most frequently discussed topics—The top N topics that the user most frequently talks about. This can be computed either by listing the top N most frequently used keywords or via statistical methods such as clustering (where the word embeddings of each word are clustered to find closely related groups of words and the most frequently used word in the cluster is then considered to be the topic of that cluster). Other methods such as Latent Dirichlet Allocation can also be used. This metric provides an estimate for the priorities of a user and changing priorities is a powerful signal of progress (i.e. if their topic of discussion moves from drug use related topics to sober living related ones). Similar to this we also collect information about their most frequently used emojis as well most frequently posted gif categories.
- Topic Specific Sentiment—For each topic that the user frequently discusses, we also compute their opinion towards that topic. This can be done by collecting every message relating to that topic and counting the number of positive opinion words and the negative opinion words and taking the difference. Another way to do it is to take the average of the message score for every message related to that topic. A shift in topic specific sentiment is also a clinically relevant marker of user mental health. An example is someone who enjoyed going to the gym but disliking it later on.
- History of User Scores—We store at any given time, the running mean & median of user scores for that day, the running mean & median of the user scores for the previous day, the running mean & median and the user scores for the current month as well as the overall mean & median of the user scores. Since a user can post multiple messages per day, this provides a baseline estimate of the user's mental health status over longer periods of time. This captures whether the user's mood has been stable or volatile.

Each of these feature vectors are concatenated to form the overall feature vector representing the user attributes 504.

The sequence of feature vectors for each message 502 along with the feature vector of the user attributes 504 are then used as inputs to a sequence prediction model 506 to predict a final user score 508 for the user. A certain amount of user activity data is required to train this user model 500. In the initial stages as the data is being collected, the overall final user score 508 can be estimated as the running mean of the individual message model scores (final prediction score 410). Once at least 3 months of user activity data has been collected it is annotated by humans who put a number to the final user score 508 (between 0-5 for example) representing the severity of the current mental health state of the user. This data is then provided to the machine learning model (which can be a structured Support Vector Machine (SVM), a Conditional Random Field or a BiLSTM neural network model) for training. As more data is collected through increased app usage, the user model can be periodically updated to provide better and more relevant predictions.

These final user scores 508 are then used in the graphical user interface to rank patients according to calculated risk. This ranking mechanism allows moderators to immediately assess which patients in the group need immediate attention and so on. The graphical interface also allows clinical users to dig deep into each patient's attributes where the previously collected metrics are collated into easily digestible reports for the moderator. For example histograms of time activity would be translated into the report as "User is most active at night" if they were most active then.

Figure 6:
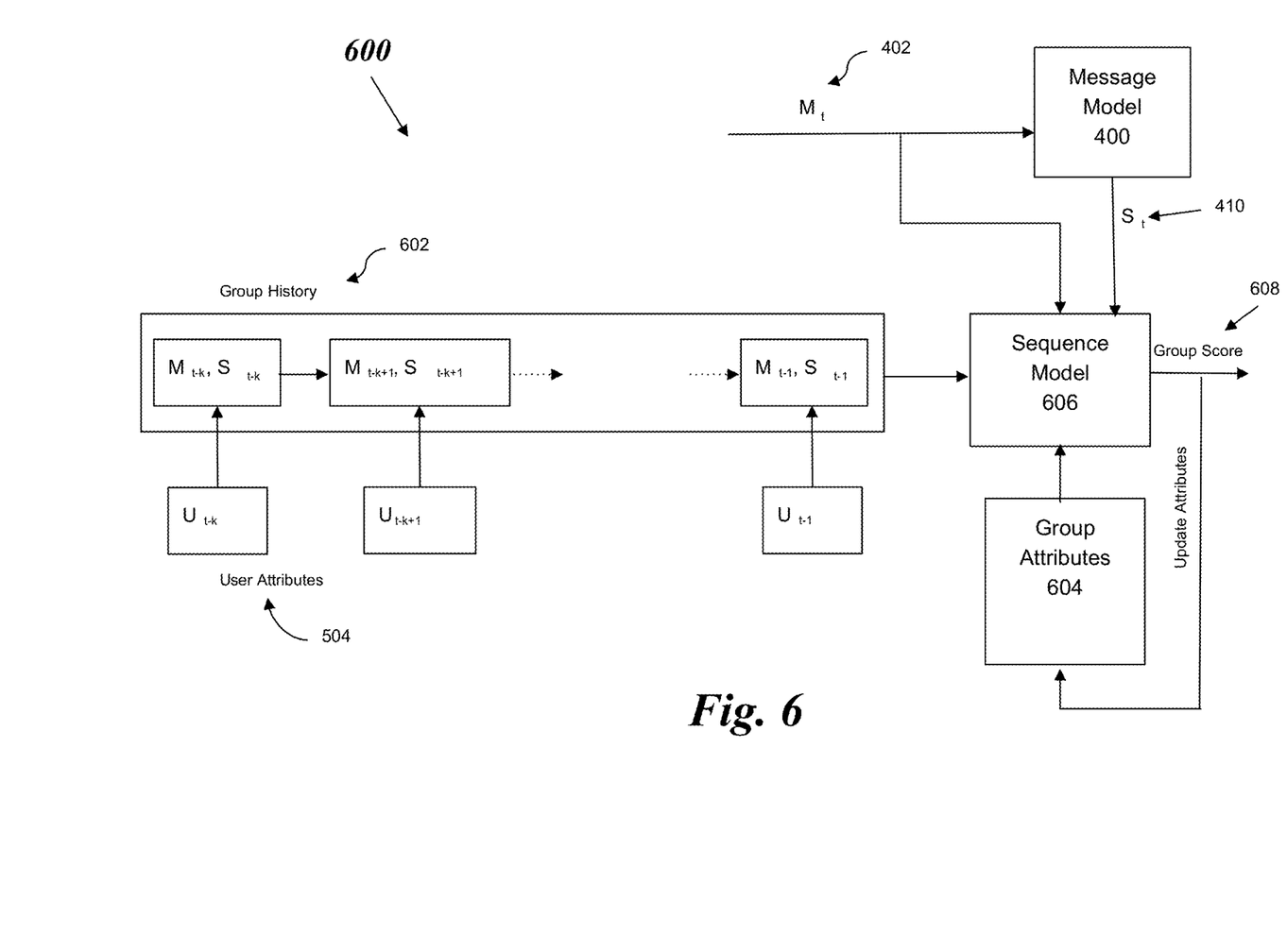
FIG. 6 is a depiction of the Group Model within the system whose purpose is to compute an overall mental health score of the group based on the context of previous messages within the group in accordance with one embodiment.

As indicted in the flow diagram of FIG. 3, the final prediction score 410 generated by the Message Model 400, the original message 402 and the final user score 508 are provided to a Group Model 600 as seen in FIG. 6.

The Group Model 600 is similar to the user score model and is used to compute the overall health of a group. The ability for a moderator to understand at a single glance the overall functioning of a group is quite powerful. This is especially relevant when they are managing multiple groups and can immediately identify the group that they need to intervene in. In addition to that there are no existing methods that quantify the overall group dynamics in a peer support group.

Every time a new message is posted in the group the score for the group is updated by the group model. The Group Model 600 takes into consideration not just the latest message but also the group history 602. The way this is done is that for each message posted by a user in the group, a database is maintained of all the messages posted in the group along with the resulting message model feature vectors, message model scores, and the user scores as encapsulated in the user attributes 504. In addition to that, a persistent set of group attributes 604 are maintained, that is updated every time a message is posted.

The list of computed group attributes include, but are not limited to, the following:

- Histogram of time activity—The time that each message is categorized into 1 of 24 hourly categories (so a message that was posted at 16:23 would fall into bucket 16) and then the total counts of each are noted. This gives the model an estimate of when users within the group most frequently post and anomalies such as late night activity can be caught. In addition to this, histograms of other sensor information, such as accelerometer data, light sensor data, and more, is also stored.

Most frequently discussed topics—The top N topics that the group most frequently talks about. This can be computed either by listing the top N most frequently used keywords or via statistical methods such as clustering (where the word embeddings of each word are clustered to find closely related groups of words and the most frequently used word in the cluster is then considered to be the topic of that cluster). Other methods such as Latent Dirichlet Allocation can also be used. This metric provides an estimate for the priorities of the group and changing priorities is a powerful signal of progress. Similar to this we also collect information about their most frequently used emojis as well most frequently posted gif categories.

Topic Specific Sentiment—For each topic that the group frequently discusses, we also compute their opinion towards that topic. This can be done by collecting every message relating to that topic and counting the number of positive opinion words and the negative opinion words and taking the difference. Another way to do it is to take the average of the message score for every message related to that topic. A shift in topic specific sentiment is also a clinically relevant marker of user mental health. For example, a shift in negative sentiment towards the therapy group itself is a substantial warning sign of a non-functioning group.

History of Group Scores—The system stores at any given time, the running mean & median of group scores for that day, the running mean & median of the group scores for the previous day, the running mean & median and the group scores for the current month as well as the overall mean & median of the group scores. Since multiple messages will be posted per day, this provides a baseline estimate of the group's mental health status over longer periods of time. This captures whether the group's mood has been stable or volatile.

User Score Vectors—A concatenated list of current users scores for every user in the group. The more number of users with low scores, the lower the group score becomes.

Interaction Networks—The total number of possible user-user interactions is enumerated (e.g. user A talks to user B). For example if there are N users, there can be N*(N-1) directed user combinations. A vector of this length is built and then the counts of the number of times a particular user messaged the other are stored as the values of that vector. These counts are then normalized by dividing them all with the total number of interactions (This is because as the number of messages increase we don't want the counts to constantly increase). This represents the nature of group interaction among users within the groups and a well balanced group should have equal interaction among each other. Within the chat application there are multiple ways these user to user interactions can be tracked and counted.

a. The first is via the @ feature of the application. Users can tag any user they want to call out in the group via the @ username feature. This automatically gives a count of user to user interactions.

b. In cases where this isn't used the central topic of every message is identified and within discrete chunks of time the first message related to that topic is considered to be the root and all the responses afterwards are considered to be directed to the user who posted the root message, unless an @ was specifically used. The topic of a message is considered to be the word within that message that is a topic from the group attributes. If multiple such words exist, then the word with the highest frequency in the group is picked to be the topic.

Interaction weights—This is a feature vector similar to the Interaction Networks but instead of counts of interactions, the values of the vectors are the average of the message scores of the message in that interaction. This is a means to capture not just how often users talk to each other but also the nature of that interaction. A healthy group would have more positive interaction weights and so on. In addition we can also build a similar vector for the median of the message scores across each user-user interaction and then concatenate it with the previous vector.

Group closeness—The closeness of the group can estimated by a metric know as generalized clustering coefficient. The metric is defined by the concept of triplets. A triplet is a set of three nodes that are connected by either 2 undirected ties (called open triplet) or 3 undirected ties (called a closed triplet). The closeness of the group can then be computed by $$g_c = \frac{\text{sum of message scores of closed triplets}}{\text{sum of message scores of all triplets}}$$

The higher the closeness of the group, the more tightly knit the interactions among them are and vice versa.

The sequence of feature vectors for each message in the group 602, including their user attributes 504, along with the feature vector of the group attributes 604 are then used as inputs to a sequence prediction model to predict a final score 608 for the group. A certain amount of activity data within a group is required to train the Group Model 600. In the initial stages as the data is being collected, the overall group score can be estimated as the running mean of the individual message model scores as well as the group closeness. Once at least 3 months of activity data has been collected it is annotated by humans who put a number to the group score (between 0-5 for example) representing the current mental health state of the group. This data is then provided to the machine learning model (which can be a structured SVM, a Conditional Random Field or a BiLSTM neural network model) for training. As more data is collected through increased app usage, the group model can be periodically updated to provide better and more relevant predictions.

Referring back to FIG. 3, the final user score 508 generated by the User Model 500 (block 306), and the score 608 generated by the Group Model 600 (block 308) is provided as a time series input to the score forecasting model (block 310). Initially, in the absence of any training data forecasts are computed by a simple drift model:

$$s_{t+x} = s_t + x\left(\frac{s_t - s_1}{t - 1}\right)$$

Where $s_t$ is the score at time t, $s_1$ is the first score and $s_{t+x}$ is the score x instances ahead of t.

With about 3 months of usage within the application any time series forecasting method, such as Long Short-Term Memory (LSTM) forecasting model can be trained.

Finally the scores computed by each of the three models are then passed to a system that makes the decision to alert the peer moderator or therapist (block 312). This could be made by a separate machine learning classifier but in other embodiments, an alert is raised if the score computed by any one of the models is below some threshold. This threshold is adjusted dynamically per group and can even be manually set by the group moderators via a moderator device 118.

In certain embodiments, users and moderators are provided the ability to flag any message they see as negative or requiring intervention. This provides a failsafe in the system to work in case the algorithms fail to properly score the message. This feature can also be used as a way to validate and improve the various models. If a message doesn't get flagged by the models, but if a user marks it as requiring intervention, that datapoint can be used to improve all of the three models.

The results of these scoring models are displayed to group moderators via a graphical user interface (GUI) provided to the moderator device 118. The GUI is available both on the mobile application as well as a separate web based dashboard. Examples of the application interface can be seen in FIG. 7a-b and an example of the web based dashboard can be seen in FIG. 8.

Figures 7A, 7B:
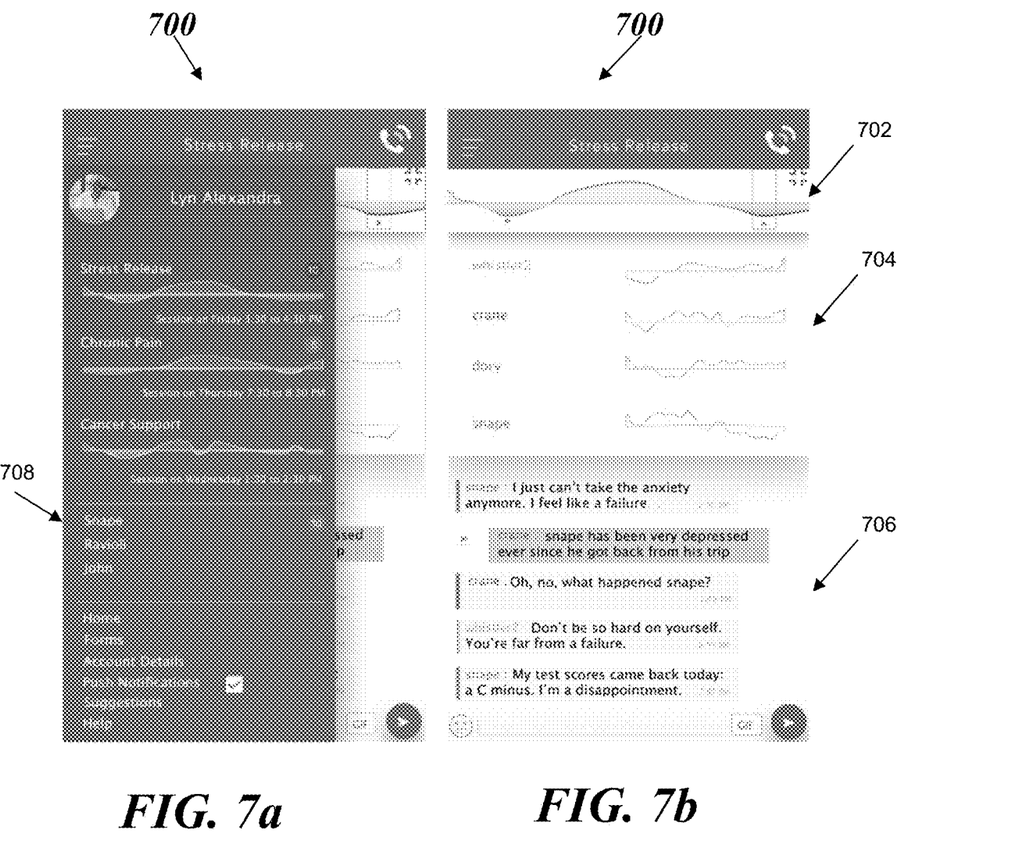
FIGS. 7a and 7b are depictions of a application graphical interface provided by the system indicating health of users and groups in an application running on moderator device in accordance with one embodiment.

The exemplary GUI 700 of FIGS. 7a-b is configured to provide data about a relevant group (in this case "Stress Release"). The GUI 700 has different sections that pertain to information relevant to different models. Through the GUI 700, moderators can visualize graphs of the group scores 702, user scores 704 as well as user forecast scores. There is also a separate section 706 that lists all the messages that raised alerts in the system.

In FIG. 7a, a menu 708 is depicted providing addition features for the moderator. In this example, groups scores for other groups the moderator monitors, users in group, and other settings and options are provided in the menu 708. In certain embodiments, the moderator can select one of the listed groups users to get more information and/or options about the group or users.

Figure 8:
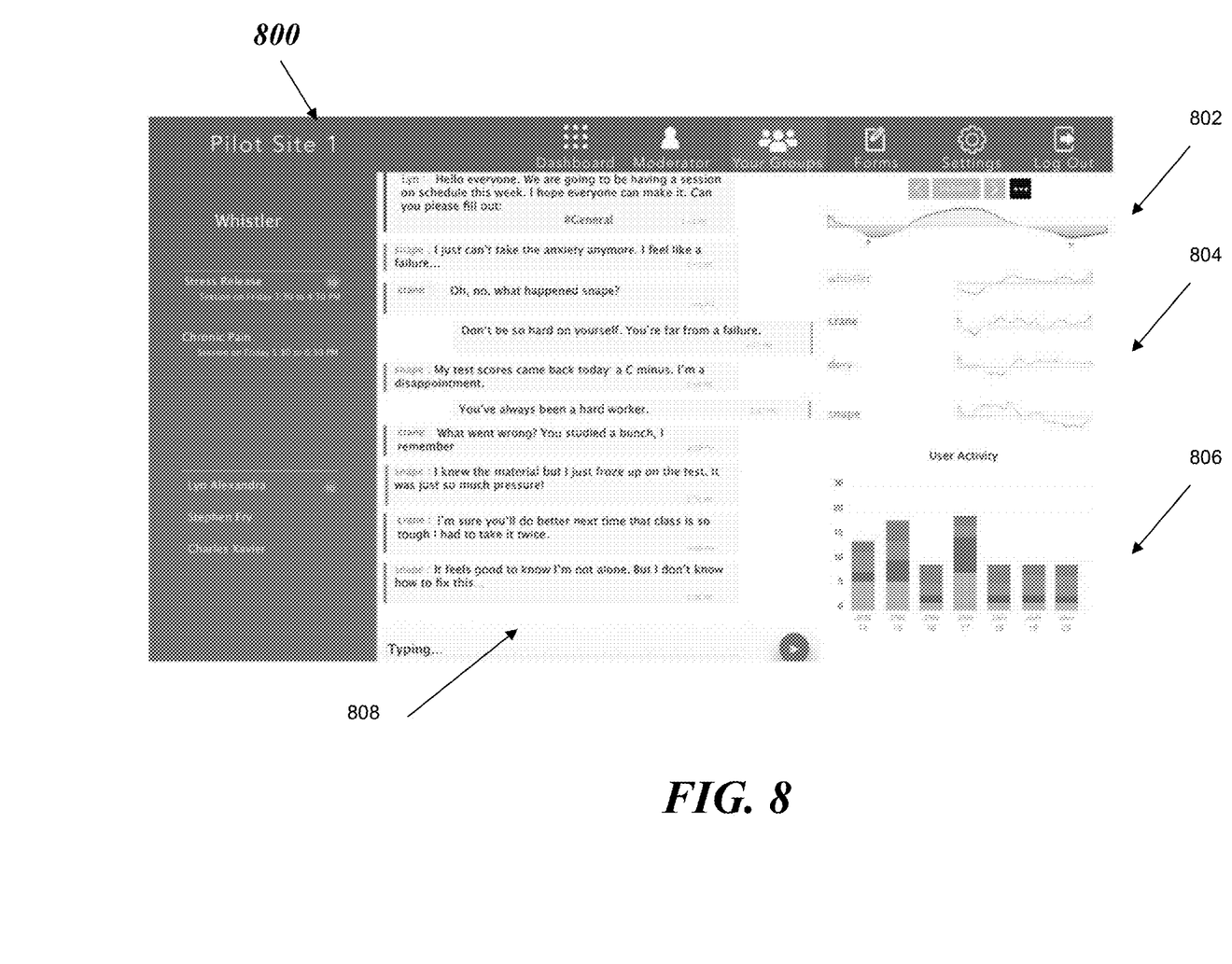
FIG. 8 is a depiction of a web based graphical interface provided by the system indicating health of users and groups in and internet browser in accordance with one embodiment.

In the exemplary web based GUI 800 of FIG. 8, moderators can visualize graphs of the group scores 802, user scores 804 as well as user activity 806. There is also a separate section 808 that shows the ongoing group chat.

Moderators have the option with the both the application and web based dashboards to customize the data being displayed. They also have the option to show only the scores between certain date ranges as well as collate it to a daily score trend, or a monthly score trend.

In certain embodiments, the moderator is provided with a section where every interaction by the moderator, whether it is a message that they sent or an activity discussion that they led, is highlighted. The moderator is then presented with score trends for each user and the group between those interaction points. In addition to that the moderator can also see the number of responses (per user and across the group) that each interaction received. This allows moderators to easily identify interventions that they performed which led to improved scores across users and groups as well the kinds of activities that drive engagement with the support group.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method for quantifying mental health for user in a group chat, the method comprising:
   receiving, at a hosting site, a message from a user in a group chat on a client device;
   processing, at the hosting site, the received message using a message model to generate a message score;
   processing, at the hosting site, the received message, the generated message score, historical data for the user, and user attributes using a user model to generate a user score;
   processing, at the hosting site, the received message, the generated message score, the generated user score, historical data for the group chat, and group attributes using a group model to generate a group score;
   determining, at the hosting site, if a moderator needs to be alerted based on the generated message score, generated user score, and generated group score; and providing to a moderator, a graphical interface indicating the generated message score, generated user score, and generated group score.

2. The method of claim 1, further comprising:
generating, at the hosting site, a user score forecast base on generated user score and generated group score; and
providing the generated forecast to the moderator as part of the graphical interface.

3. The method of claim 1, further comprising:
receiving, at the hosting site, an indication that a message has been flagged;
determining, at the hosting site, if the flagged message is a message that led to a determination that a moderator need to be alerted; and
updating models if flagged message did not result in moderator being alerted.

4. The method of claim 1, wherein historical data for the user comprises previous messages from the user, the corresponding user scores for the messages, and message feature vectors for the messages used in generating the user scores.

5. The method of claim 1, wherein historical data for the group chat comprises previous messages for all the users in a group, the corresponding messages scores, message feature vectors for the messages used in generating the user scores, and the resulting group scores.

6. The method of claim 1, wherein generating a message score comprises:
applying a group of one or more transformations to the message to generate a set of one or more vectors pertaining to the message;
concatenating the set of one or more vectors pertaining to the vector into a message feature vector; and
applying a classifier to the message feature vector to generate a message score.

7. The method of claim 6, wherein applying a group of one or more transformations to the message comprises:
applying a first group of one or more transformations to the message to generate a first set of one or more vectors pertaining to the message;
concatenating the first set of one or more vectors pertaining to the message into a first feature vector;
applying a second group of one or more transforms to the first feature vector to generate a second set of one or more vectors pertaining to the message; and
concatenating the second set of one or more vectors pertaining to the message into a message feature vector.

8. The method of claim 1, wherein generating a user score comprises:
applying one or more transformations on the message, message score, and user history to generate a set of one or more vectors pertaining to the user;
concatenating the set of one or more vectors pertaining to the user to generate a user attributes vector; and
inputting the message, message score, user history, and user attributes vector into a sequence prediction model to generate a user score.

9. The method of claim 1, wherein generating a group score comprises:
applying one or more transformations on the message, message score, user score, and history of group to generate a set of one or more vectors pertaining to the group;
concatenating the set of one or more vectors to generate a group attributes vector; and
inputting the message, message score, group history, and group attributes vector into a sequence prediction model to generate a group score.

10. A system for quantifying mental health for user in a group chat, the system comprising:
a hosting site comprising a storage for storing messages from users and data associated with messages, the hosting site operable to:
receive a message from a user in a group chat on a client device;
process the received message using a message model to generate a message score;
process the received message, the generated message score, historical data for the user, and user attributes using a user model to generate a user score;
process the received message, the generated message score, the generated user score, historical data for the group chat, and group attributes using a group model to generate a group score;
determine if a moderator needs to be alerted based on the generated message score, generated user score, and generated group score; and
provide to a moderator, a graphical interface indicating the generated message score, generated user score, and generated group score.

11. The system of claim 10, wherein the hosting site is further operable to:
generate a user score forecast base on generated user score and generated group score; and
provide the generated forecast to the moderator as part of the graphical interface.

12. The system of claim 10, wherein the hosting site is further operable to:
receive an indication that a message has been flagged;
determine if the flagged message is a message that led to a determination that a moderator need to be alerted; and
update models if flagged message did not result in moderator being alerted.

13. The system of claim 10, wherein historical data for the user comprises previous messages from the user, the corresponding user scores for the messages, and message feature vectors for the messages used in generating the user scores.

14. The system of claim 10, wherein historical data for the group chat comprises previous messages for all the users in a group, the corresponding messages scores, message feature vectors for the messages used in generating the user scores, and the resulting group scores.

* * * * *